(12) United States Patent
Tillman

(10) Patent No.: US 9,349,268 B2
(45) Date of Patent: May 24, 2016

(54) TNT-MEDICAL ALERT SYSTEM

(71) Applicant: Cornelius Tillman, Melbourne, FL (US)

(72) Inventor: Cornelius Tillman, Melbourne, FL (US)

(*) Notice: Subject to any disclaimer, the term of this patent is extended or adjusted under 35 U.S.C. 154(b) by 0 days.

(21) Appl. No.: 14/611,221

(22) Filed: Mar. 2, 2015

(65) Prior Publication Data

US 2015/0356800 A1 Dec. 10, 2015

Related U.S. Application Data

(60) Provisional application No. 62/009,290, filed on Jun. 8, 2014.

(51) Int. Cl.
*G08B 1/08* (2006.01)
*G08B 21/02* (2006.01)
*G08B 21/04* (2006.01)
*G08B 25/01* (2006.01)

(52) U.S. Cl.
CPC .............. *G08B 21/02* (2013.01); *G08B 21/043* (2013.01); *G08B 21/0446* (2013.01); *G08B 25/016* (2013.01)

(58) Field of Classification Search
CPC .............. G08B 21/02; G08B 21/0446; G08B 21/0453; G08B 21/43; G08B 25/016; G08B 21/043
USPC .......... 340/539.12, 693.6, 532, 693.5, 539.1, 340/573.1, 573.4, 573.7, 539.11; 600/595; 382/103
See application file for complete search history.

(56) References Cited

U.S. PATENT DOCUMENTS

| 8,120,481 B2* | 2/2012 | Gottlieb | G08B 25/016 340/532 |
| 8,400,268 B1* | 3/2013 | Malik | G06Q 10/06 340/539.12 |
| 2008/0001735 A1* | 1/2008 | Tran | G06F 19/3418 340/539.22 |
| 2012/0314901 A1* | 12/2012 | Hanson | A61B 5/1117 382/103 |
| 2014/0253324 A1* | 9/2014 | Tamez | A61B 5/1135 340/539.12 |

* cited by examiner

*Primary Examiner* — Ahn V La
(74) *Attorney, Agent, or Firm* — Cornelius Tillman; Theodore Alexander

(57) ABSTRACT

The inventive device object of the present application is a comprehensive medical alert system that will save the lives of many people. When immediate medical attention is needed to save a life or to reduce complications, first responders need prompt access to the patient when they arrive at the patient's home. When the door is unlocked automatically using this system, medical personnel will be able to attend to the patient more quickly. It is emphasized that this abstract is provided to comply with the rules requiring an abstract that will allow a searcher or other reader to quickly ascertain the subject matter of the technical disclosure.

1 Claim, 3 Drawing Sheets

TNT-MEDICAL ALERT SYSTEM

BACKGROUND OF THE INVENTION

1. Field of the Invention

The inventive device disclosed in the present application generally relates to medical alert systems and more specifically to a comprehensive medical alert system that will save the lives of many people. The inventor commonly refers to it as the TNT-Meduical Alert System. When immediate medical attention is needed to save a life or to reduce complications, first responders need prompt access to the patient when they arrive at the patient's home.

2. Brief Description of the Prior Art

Medical Alert systems are well known in the art. For example, U.S. Pat. No. 8,348,839 to Sharda and Linthicum discloses and claims a method of monitoring an environment comprising: monitoring at least one data stream wherein the data stream is a data stream in the environment; detecting a specified event from the data stream; and triggering a response to the specified event. Embodiments of the Sharda and Linthicum invention provide a system for monitoring an environment comprising: a receiver adapted to receive at least one input data stream wherein the input data stream is a data stream in the environment; an active listener/observer system adapted to monitor the data stream; and an interface adapted to express at least one output stream. Embodiments of the Sharda and Linthicum invention provide a computer-readable readable medium having instructions comprising: an active listener/observer routine configured to monitor at least one data stream; a detection routine configured to find specified events in the data stream; and an output routine configured to express a response event.

In addition to that, U.S. Pat. No. 8,169,315 to Smith and Mikan discloses and claims, a device and method for sending medic alert information electronically. The Smith and Mikan device may have a memory component and a processing component. The memory component may store medic alert information. The processing component may generate an electronic message containing the medic alert information and send the electronic message via a communications network. The Smith and Mikan device may also have an input component for receiving a user request to initiate a connection with an emergency contact, such as a 911 dispatcher. The electronic message may be automatically generated and sent in response to the user request.

U.S. Pat. No. 7,138,902 to Menard discloses and claims, a personal and/or institutional health and wellness communications system, which may be used for a variety of emergency and non-emergency situations using two-way communication devices and a bi-directional communication network. In one application of the Menard invention two-way pagers are adapted for use in the system. In one application cellular devices are adapted for use in the system. In one application an assisted living response center is established using various embodiments of the present personal and/or institutional communications system. The system disclosed by Menard's patent, provides multiple levels of prioritization, authentication of person (task, step, process or order), and confirmation via interrogation of person, device, or related monitor. One embodiment provides a method for receiving, evaluating and responding to calls received from a subscriber, patient, related party, or health care provider or health care system.

U.S. Pat. No. 4,237,344 to Moore discloses and claims, a rapid response health care communications system for providing rapid and reliable health services to patients located within or outside a health care facility, such as an acute-care hospital, includes personnel locator for identifying both the type and the location of health care personnel, such as doctors, nurses, interns, and the like; and personnel communicating network for communicating with certain of such personnel from a central location to direct them to patient locations where their need is paramount. A patient response communication network is provided for communicating with the patient or with the patient's room from the central location to identify the patient's needs and the personnel required to respond to those needs. A central console at the central location includes a plurality of locator panels, one for each floor of the facility, each of which include indicator lamps for identifying the particular location of the health care personnel within the facility. The console further includes a device for storing and retrieving a patient's medical profile to assist the health care coordinator in making an informed judgment as to the type of care required for a particular patient and the type of health care personnel needed to provide the required care. In addition, an out-of-hospital communication network using auto-dialing telephones is provided to allow outpatients to communicate from outside the facility with the health care coordinator to assist the outpatients in rapidly and efficiently receiving appropriate advice and health care as indicated by the patient medical profile and for responding to emergency situations.

Finally, U.S. Published Patent Application No. 20090322513 to Hwang and Huang discloses, a medical emergency reporting system and methodology that utilize a wearable monitoring device to continuously monitor key physiological parameters of a person, and when measurements exceed programmed threshold levels, it will automatically issue a medical emergency alert along with location information to a remote monitoring center via a wireless network and the Internet for immediate local response. The Hwang and Huang system will also provide manual emergency alert activation, continuous updates with key physiological measurements to the emergency response personnel along with the medical history of the subject as well as redundancy in emergency alert reporting and malfunction diagnosis to assure ultimate accuracy, immediacy and reliability for the person that requires medical assistance.

Despite all the efforts listed above prior art patents describe structures that are either not truly convenient or else involve complicated, expensive, and overly difficult assembly and/or disassembly parts and procedures. Other devices have been advertised on various media but never patented or described into a printed publication.

SUMMARY OF THE INVENTION

The invention is a comprehensive medical alert system that will save the lives of many people. When immediate medical attention is needed to save a life or to reduce complications, first responders need prompt access to the patient when they arrive at the patient's home. When the door is unlocked automatically using this system, medical personnel will be able to attend to the patient more quickly.

It is then the principal object of the present invention is to provide immediate access to medical personnel when needed. It is a secondary objective of the present invention to eliminate the need to scramble to unlock a lock box, to wait for someone with a key, or to break into the home.

It is an additional objective of the present invention to provide a device that does not deteriorate over time causing longer delays for first responders to locate the emergency. It is a final objective of the present invention to provide for a device that is relatively inexpensive to built and set up, but can eventually be sold at a premium.

These and other objective achieved by the device of the present invention will be apparent by the drawings, by their detailed description, and by the specification here from appended.

DESCRIPTION OF THE PREFERRED EMBODIMENT

Figure 1:
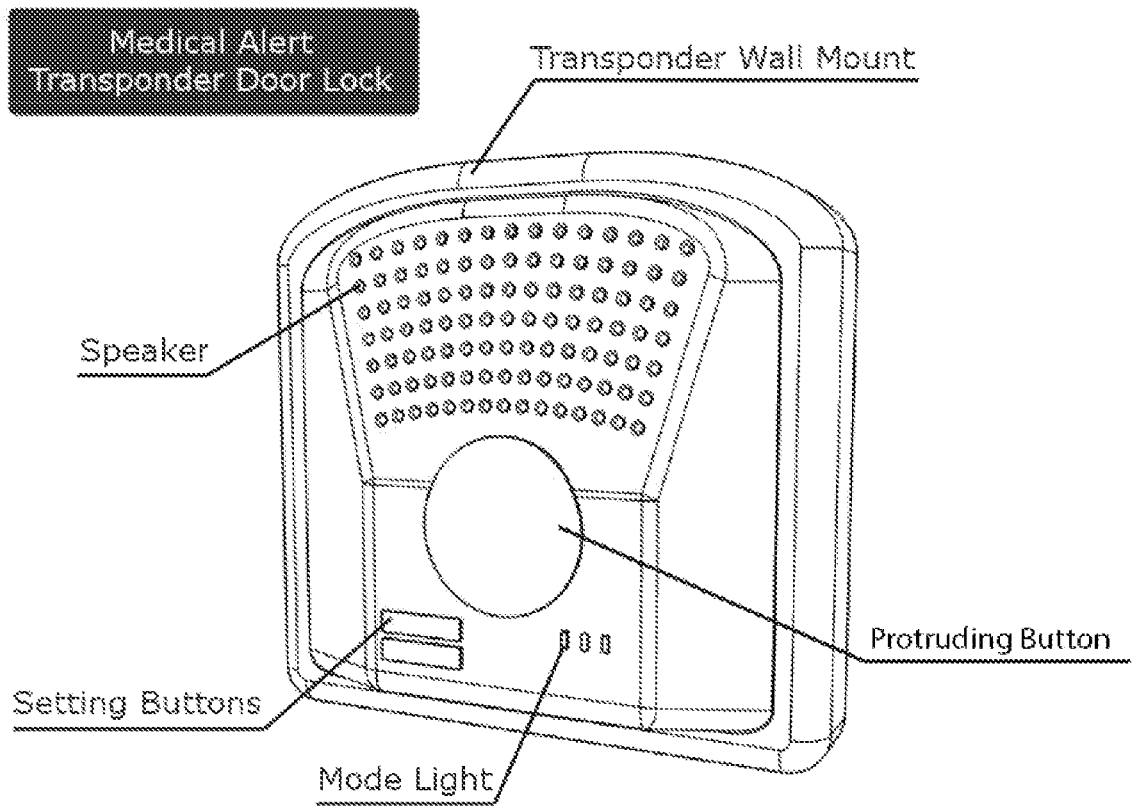
FIG. 1 is a perspective view of "TNT-Medical Alert System" in accordance with the teaching of the present invention.
Figure 2:
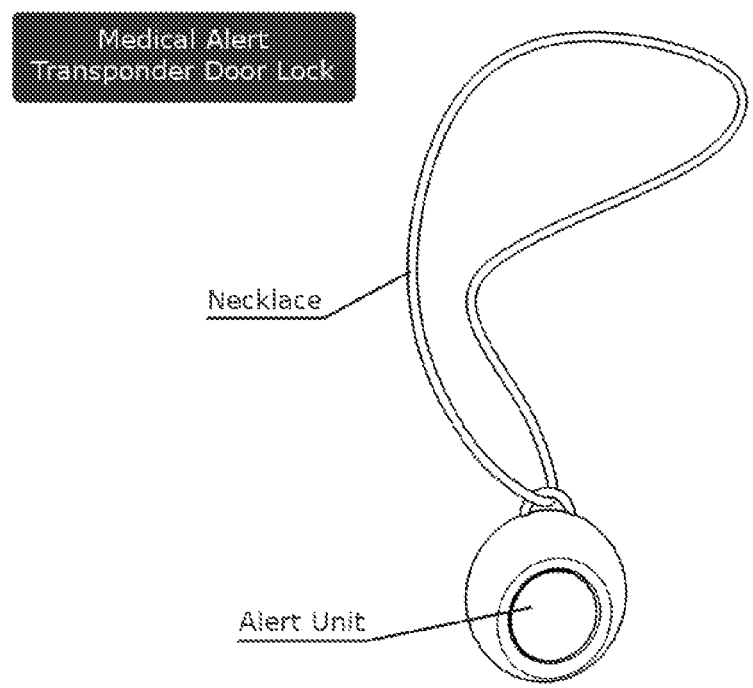
FIG. 2 is a perspective view of "TNT-Medical Alert System" necklace and all its features.
Figure 3:
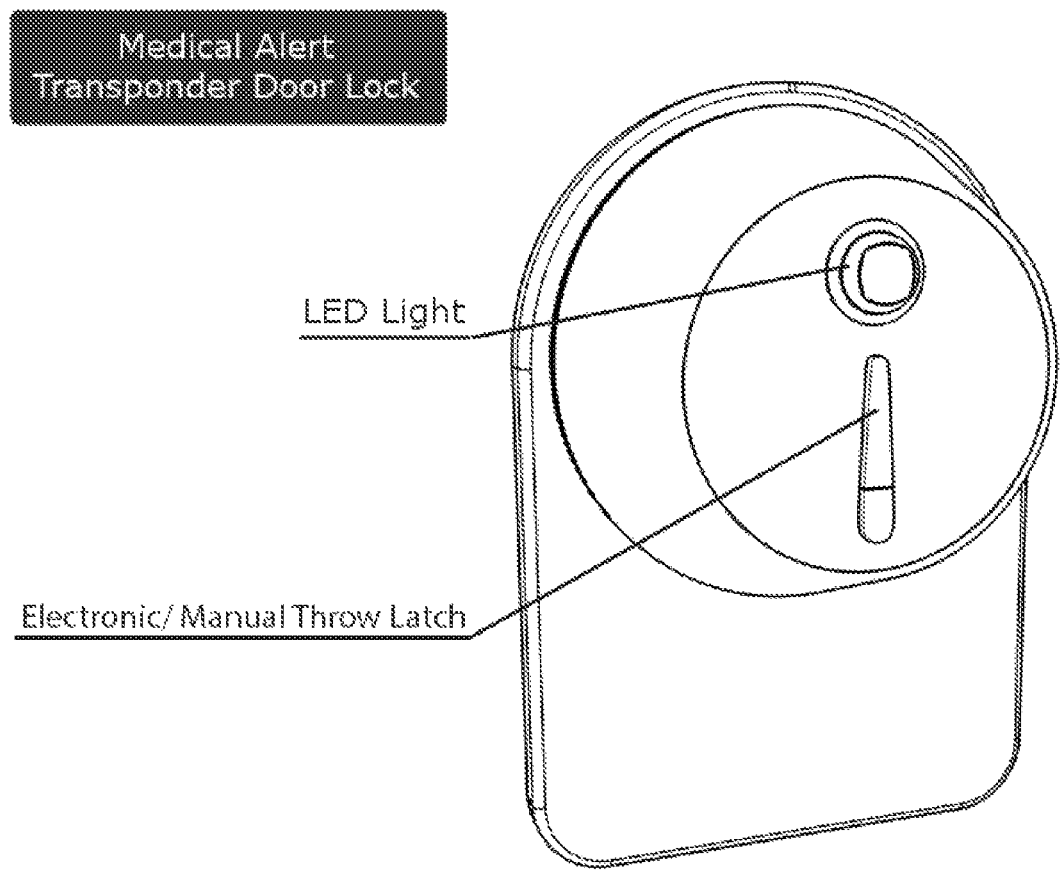
FIG. 3 is a perspective view of "TNT-Medical Alert System" of FIG. 1.

The invention is a comprehensive medical alert system that will save the lives of many people. When immediate medical attention is needed to save a life or to reduce complications, first responders need prompt access to the patient when they arrive at the patient's home. When the door is unlocked automatically using this system, medical personnel will be able to attend to the patient more quickly. As it can be inferred from the drawings essential components of the "TNT-Medical Alert System"of the present application include: a transponder wall mount, a speaker, a mode light, a setting button, a necklace, an alert unit, a LED light, an electronic/manual throw latch, and a protruding button.

For the purpose of the present application a LED is a light-emitting diode: a semiconductor light source. LEDs are used as indicator lamps in many devices and are increasingly used for other lighting. Appearing as practical electronic components in 1962, early LEDs emitted low-intensity red light, but modern versions are available across the visible, ultraviolet, and infrared wavelengths, with very high brightness.

The TNT-Medical Alert System is similar to all medical alert systems as it provides a way to send a signal to a response station that a client is in need of help. This system consists for four units. There is a wall-mounted unit that can be actuated manually, and it has an intercom so the client can speak with the personnel at the station. A personal necklace is equipped with a fall detection sensor, which sends a signal to the call center automatically even when the client is unable to push a button.

A pocket unit provides the same service as the personal necklace. When any of these three units is actuated, a signal is sent automatically to the remote door lock to unlock the door so first responders can come directly into the home. The remote door lock can work independently without activating the response feature. The client can lock and unlock the door manually. With the door lock actuation is always in the open position, the circuit is not complete until one of the units sends out a response signal. The system can be reset using the wall-mounted unit.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A personal medical alert system comprising:
   (a) a wall mount unit that sends a signal to a remote door lock to unlock and to a monitoring station that is staffed with operators to summon 1st responders to a clients home or apartment;
   (b) a personal pendant/necklace that sends a signal to the remote door lock to unlock upon falling to unlock and to the wall mount unit that causes a signal to be sent to the monitoring station to summon the 1st responders to the clients home or apartment;
   (c) a remote door lock that receives the signal from the pendant/necklace and the signal from the wall mount unit to unlock whereas the signal is sent to the monitoring station to summon the 1st responders to the clients home or apartment;
   (d) the wall mount unit that can be used independently without activating the signal for the 1st responders;
   (e) the wall mount unit that provides a two way communication between the monitoring station and clients without activating the remote door lock;
   (f) a circuitry in the wall mount unit that is configured with a switchable analog and digital phone signal;
   (g) the remote door lock that receives a sensing signal from a fall detection sensor located in the pendant/necklace to unlock;
   (h) wherein the medical alert system further consists of information at the monitoring station to give to the 1st responders including family, medical information and client address;
   (i) the pendant/necklace that includes an alert button and is equipped with a circuitry that provides fall detection when the client cannot press the alert button;
   (j) the wall mount unit that is equipped with an intercom for communication with the monitoring station for emergency and non-emergency calling; and
   (k) the remote door lock that allows the 1st responders immediate access to the clients home or apartment when the 1st responders arrive without having to find a key.

* * * * *